(12) United States Patent
Haberman et al.

(10) Patent No.: US 11,166,713 B2
(45) Date of Patent: Nov. 9, 2021

(54) SIDE LOADING KNOT CUTTER

(71) Applicant: Smith & Nephew, Inc., Memphis, TN (US)

(72) Inventors: Daniel Haberman, Boston, MA (US); Stephen Santangelo, Sturbridge, MA (US)

(73) Assignee: SMITH & NEPHEW, INC., Memphis, TN (US)

( * ) Notice: Subject to any disclaimer, the term of this patent is extended or adjusted under 35 U.S.C. 154(b) by 262 days.

(21) Appl. No.: 16/539,051

(22) Filed: Aug. 13, 2019

(65) Prior Publication Data

US 2019/0357903 A1      Nov. 28, 2019

Related U.S. Application Data

(62) Division of application No. 15/513,202, filed as application No. PCT/US2015/051413 on Sep. 22, 2015, now Pat. No. 10,426,462.

(60) Provisional application No. 62/055,049, filed on Sep. 25, 2014.

(51) Int. Cl.
   *A61B 17/04*      (2006.01)

(52) U.S. Cl.
   CPC .......... *A61B 17/0469* (2013.01); *A61B 17/04* (2013.01); *A61B 17/0467* (2013.01); *A61B 2017/0474* (2013.01); *A61B 2017/0475* (2013.01); *A61B 2017/0477* (2013.01)

(58) Field of Classification Search
   CPC ..... A61B 17/00; A61B 17/04; A61B 17/0467; A61B 2017/0474; A61B 2017/0477; A61B 17/0469; Y10T 83/04
   See application file for complete search history.

(56) References Cited

U.S. PATENT DOCUMENTS

| | | | | |
|---|---|---|---|---|
| 8,603,125 B2 * | 12/2013 | Stone | .................. | A61B 17/0469 606/170 |
| 2011/0100173 A1 * | 5/2011 | Stone | .................. | A61B 17/0482 83/13 |
| 2011/0106106 A1 * | 5/2011 | Meier | ................ | A61B 17/0469 606/139 |

* cited by examiner

*Primary Examiner* — George J Ulsh
(74) *Attorney, Agent, or Firm* — Burns & Levinson, LLP; Joseph M. Maraia

(57) ABSTRACT

An instrument for securing a knot disposed in surgical suture is provided. The instrument includes a side-loading channel disposed along the side of a knot pusher, the side-loading channel configured to receive the suture into the knot pusher. A method of operation is disclosed.

12 Claims, 5 Drawing Sheets

SIDE LOADING KNOT CUTTER

CROSS-REFERENCE TO RELATED APPLICATIONS

This application is a divisional of co-pending U.S. application Ser. No. 15/513,202, which in turn is the U.S. National Phase entry under 35 U.S.C. § 371 of International Application No. PCT/US2015/051413 filed Sep. 22, 2015, entitled SIDE LOADING KNOT CUTTER, which in turn claims the benefit of U.S. Provisional Application No. 62/055,049, filed Sep. 25, 2014, the entire contents of which are hereby incorporated by reference herein for all purposes.

BACKGROUND OF THE INVENTION

1. Field of the Invention

The invention disclosed herein relates to a surgical instrument, and, in particular, an instrument for securing suture.

2. Description of the Related Art

Surgeons are continually faced with challenges as non-invasive surgical techniques continue to improve. While the use of a smaller incision will substantially benefit patient recovery, effective manipulation of tissue and surgical instruments becomes more complicated. Consider, for example, how tying of knots within a surgical site can foreseeably become very difficult.

Accordingly, a number of tools have been developed to assist securing of suture within arthroscopic operations. Some tools make use of needles or needle like structures to carry the suture. As one might imagine simply loading such a tool during an operation can be a challenge, let alone using such a tool.

Thus, what are needed are methods and apparatus to provide simplified techniques for securing of a suture. Preferably, the methods and apparatus provide for simplified preparation as well as remote manipulation of surgical knots.

SUMMARY OF THE INVENTION

In one embodiment, an instrument for securing a knot disposed in surgical suture is provided. The instrument includes a side-loading channel disposed along the side of a knot pusher, the side-loading channel configured to receive the suture into the knot pusher.

In another embodiment, a method for securing a suture including a knot is provided. The method includes: selecting an instrument including a side-loading channel disposed along the side of a knot pusher, the side-loading channel configured to receive the suture into the knot pusher; loading the suture into the side-loading channel; and pushing the knot pusher to secure the suture.

In yet another embodiment, an instrument for securing a knot disposed in surgical suture is provided. The instrument includes: a side-loading channel including a helical pattern that is disposed along the side of a knot pusher, the side-loading channel configured to receive the suture into the knot pusher; wherein the knot pusher includes a cannulated tip for receiving the suture from the side-loading channel and is configured to retain the slip knot in knot retainer disposed in a distal tip thereof; wherein the cannulated tip includes a cutting surface for cutting the suture; and, a cutting sleeve disposed over the knot pusher with a user manipulable control for controlling the cutting sleeve and sliding the cutting sleeve over the knot pusher; the cutting sleeve including a knife for cutting the suture and at least one vent configured to pass debris.

BRIEF DESCRIPTION OF THE DRAWINGS

The features and advantages of the invention are apparent from the following description taken in conjunction with the accompanying drawings in which.

DETAILED DESCRIPTION OF THE INVENTION

Disclosed herein is a side-loading knot pusher and suture cutter. Generally, the side-loading knot pusher and suture cutter facilitates the securing of suture containing a knot. Accordingly, the side-loading knot pusher and suture cutter greatly improves the efficiency of a surgeon using the instrument, and further reduces fatigue induced by tedious processes such as attempting to thread a suture.

Figure 1:
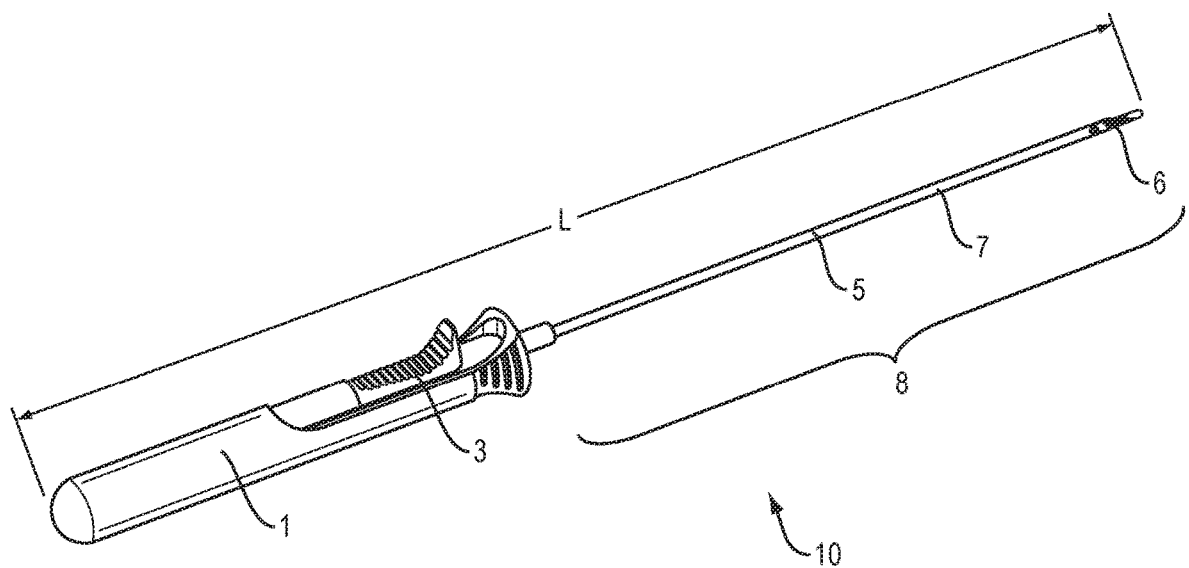
FIG. 1 is an isometric diagram depicting a side loading knot pusher and suture cutting instrument.

Referring now to FIG. 1, there is shown an exemplary embodiment of a side-loading knot pusher and suture cutter, hereafter referred to simply as "instrument" 10. In this example, the instrument 10 includes handle 1 and shaft 8. For purposes of discussion, it is considered that the handle 1 is proximal, while the shaft is distal. Generally, such orientation is consistent with how the instrument 10 will be deployed during surgery. However, terms of geometry are not to be construed as limiting of the teachings herein.

Disposed within the handle 1 is a control 3. Generally, the control 3 provides for manipulation of a cutting sleeve 5. The cutting sleeve 5 is disposed as an outer sleeve over an inner shaft, referred to herein as "knot pusher" 7. Together, knot pusher 7 and cutting sleeve 5 form the shaft 8. At a distal tip of the shaft 8 is side-loading tip 6. Design of the side-loading tip 6 is such that a surgeon may very quickly and efficiently capture suture and secure a knot that is disposed within the suture (the suture and the knot therein are not shown in this disclosure).

As discussed herein, the suture includes a slip knot disposed therein. However, this is not limiting of the teachings herein. For example, the suture may include a one-way slidable knot, an adjustable knot, or any other kind of knot deemed appropriate. Generally, the nature of the knot is to be judged by the user (e.g., a surgeon) or another similarly situated party.

Figure 2A:
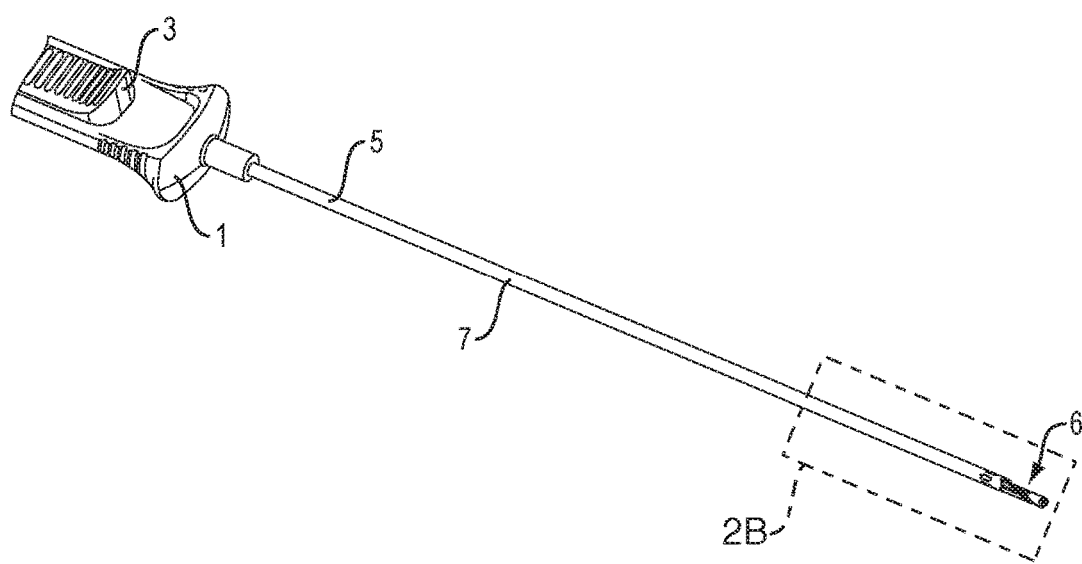
FIGS. 2A and 2B, collectively referred to herein as FIG. 2, is an isometric view of a distal tip of the instrument of FIG. 1.
Figure 2B:
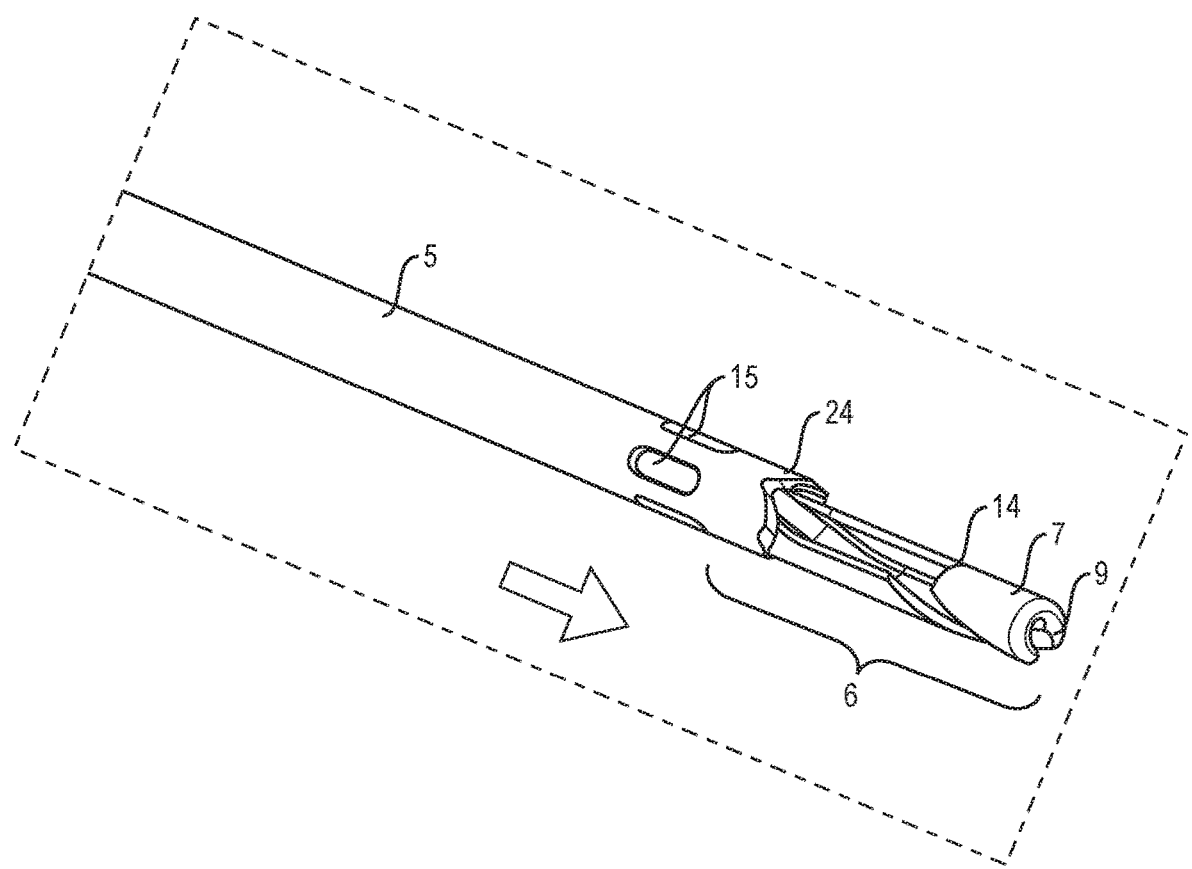

Referring now to FIG. 2, the site-loading tip 6 is shown in greater detail. FIG. 2A is provided to better orient the reader with an understanding of the geometry of the portion of the instrument 10 that is shown in FIG. 2B.

Referring to FIG. 2B, a may be seen that the distal tip of the instrument 10 includes various components to facilitate operation of the instrument 10. Generally, cutting sleeve 5 is configured to slide in a distal direction over the knot pusher 7. Knife 24 is disposed at a distal tip of cutting sleeve 5. During operation, knife 24 will slide in the forward or distal direction as implied by the arrow depicted. By sliding knife 24 in a distal direction, knife 24 will cut the suture against cutting surface 14. Loading and retention of the suture is explained with greater detail and in view of FIGS. 3 and 4.

In this exemplary embodiment, the knot pusher 7 remain stationary relative to the handle 1, while the cutting sleeve 5 may be moved in a proximal and distal direction. However, in other embodiments, the cutting sleeve 5 remain stationary relative to the handle 1 while the knot pusher 7 may be moved in a proximal and distal direction. In some further embodiments, it is possible that the cutting sleeve 5 in the knot pusher 7 are both movable relative to the handle 1.

Figure 3:
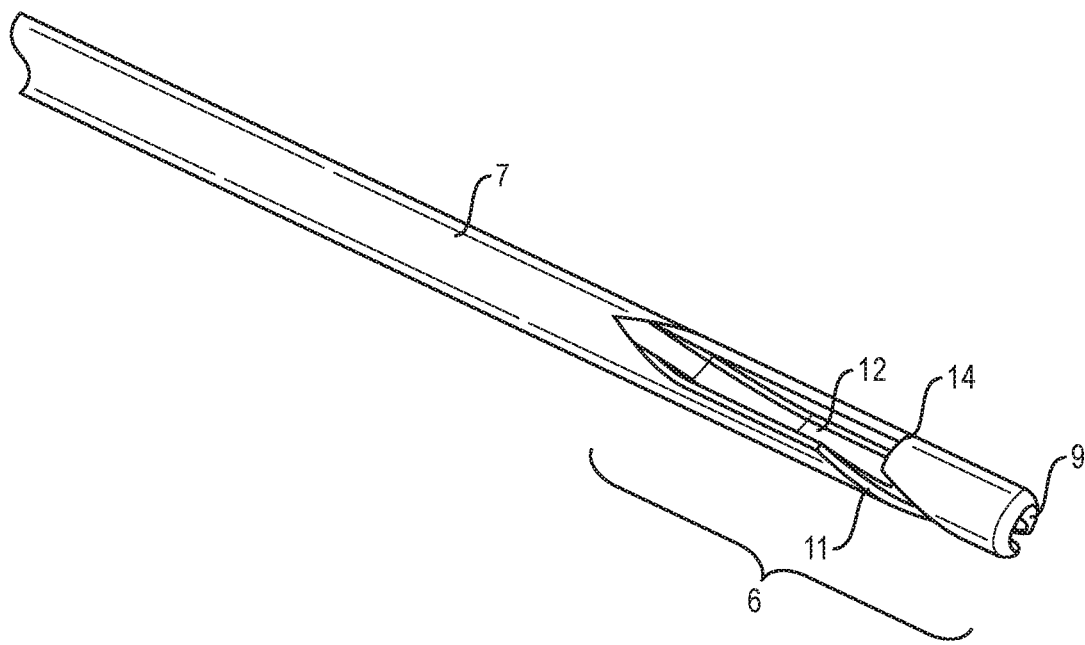
FIGS. 3 and 4 are close-up isometric views of a portion of the distal tip of the instrument of FIG. 1.

Referring now to FIG. 3, a cutaway isometric view of the knot pusher 7 is shown. In this illustration, the cutting sleeve 5 has been removed to better show the features of the knot pusher 7. In this illustration, the side-loading tip 6 includes an open cannulation 12. That is, a portion of the side wall of the knot pusher 7 has been cutaway, and exposes a cannulation 12 in the distal end of the knot pusher 7. Disposed at the distal tip of knot pusher 7 is knot retainer 9. Knot retainer 9 may be provided as a cup-shaped tip suited for retaining the knot that is disposed in the suture.

Figure 4:
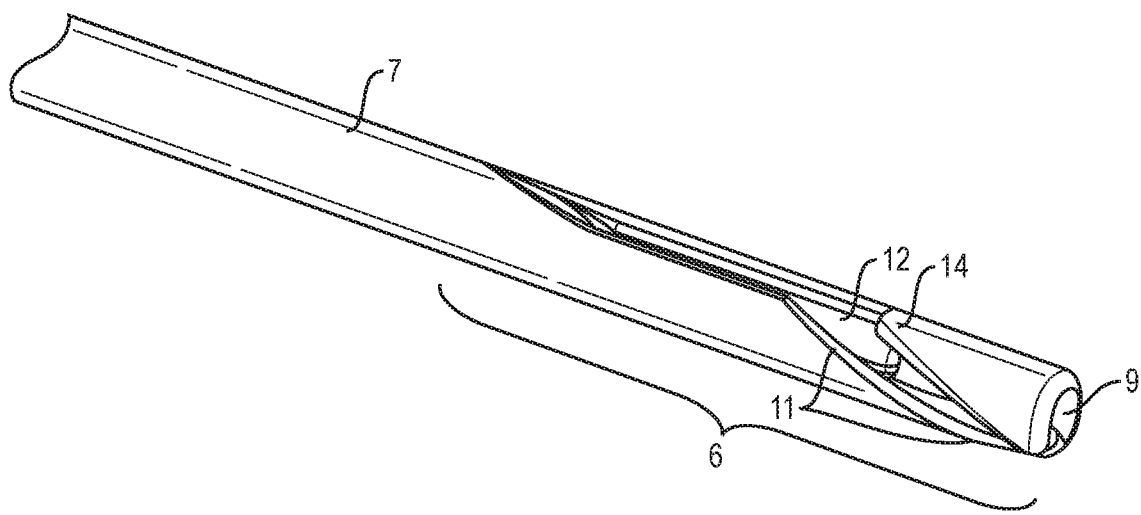

Extending around a portion of the knot pusher 7 from the cannulation 12 to knot retainer 9 is a side-loading channel 11. In this example, the side-loading channel 11 is of a helical shape that tracks a portion of the circumference of the knot pusher 7. As shown in FIGS. 3 and 4, the side-loading channel 11 is disposed in about one quarter to one third of the circumference of the knot pusher 7. FIG. 4 provides a slightly better view of the side loading channel 11.

In order to load suture into the instrument 10, the user of the instrument 10 merely needs to place a moderate tension on the suture and then either twist the suture around the side-loading tip 6, or twist the side-loading tip 6 around the suture. During this process, the suture will migrate into the side-loading channel 11. Once the suture has migrated into the side-loading channel 11, the instrument 10 may be pushed in a distal direction such that the knot disposed in the suture comes into contact with and is retained in knot retainer 9.

Once the knot has been retained in knot retainer 9, the user may guide the suture to the desired location, and then pull the suture taught such that the slip knot is tightened in place. At this point, the user will slide the control 3 and a distal direction, thus causing knife 24 to cut the suture against cutting surface 14.

In some embodiments, the cutting sleeve 5 may include optional vents 15. Generally, the vents 15 are useful for relieving pressure that may build within the cannulation as the cutting sleeve is slid forward over accumulated debris. Additionally, the vents 15 at the distal end of the cutting sleeve 5 allow the surgeon to arthroscopically view the suture within the knot pusher 7, and furthermore to provide confirmation that the suture has been cut.

Figure 5:
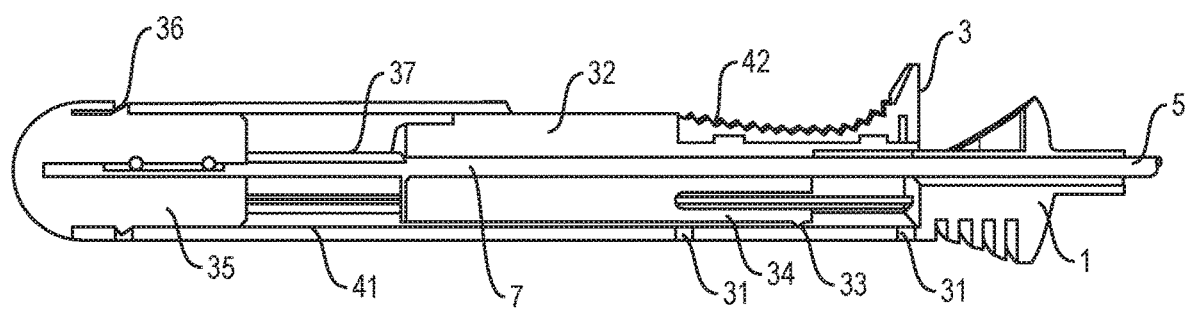
FIG. 5 is a cutaway isometric view of the handle of the instrument of FIG. 1.

Turning now to FIG. 5, a cutaway isometric view of the handle 1 is shown. In this example, the handle 1 includes a hollow, cylindrical shell 41. During the assembly process, a proximal end of the shell 41 is open. When the proximal end of the shell 41 is open, a body 32 for the control 3 is inserted within the shell 41. Disposed within the body 32 is a proximal end of the cutting sleeve 5. Generally, the body 32 may cooperate with at least one rib 37. The at least one rib 37 may be disposed along an interior surface of the shell 41. The at least one rib 37 provides for structural enhancement of the shell 41 as well as retention and guidance of the body 32 during operation.

Once the body 32 with the cutting sleeve 5 mounted therein has been inserted into the shell 41, and moved into a distal portion of the shell 41, plug 35 is then inserted into the open proximal end of the shell 41. In this example, plug 35 includes the proximal end of the knot pusher 7 disposed therein. Plug 35 may be securely mated with shell 41 by use of an interlock 36. Any type of interlocking features deemed suitable may be used for interlock 36. For example, friction fit nipples may be disposed within detents formed in the shell 41.

Generally, once body 32 has been inserted into shell 41, thumb latch 42 is affixed thereto.

In some embodiments, shell 41 further includes at least one detent for controlling motion of the control 3 in a proximal and distal direction. That is, as an example, the body 32 may include spring 34 which includes nipple 33. Spring 34 will bias nipple 33 to a distally oriented detent 31 or a proximately oriented detent 31. Accordingly, a user will be able to identify by feel whether the instrument 10 is reached a limit of motion. Further, by using a nipple 33 and detent 31, positioning of the cutting sleeve 5 relative to the knot pusher 7 may be affirmatively controlled during use of the instrument 10.

Figure 6:
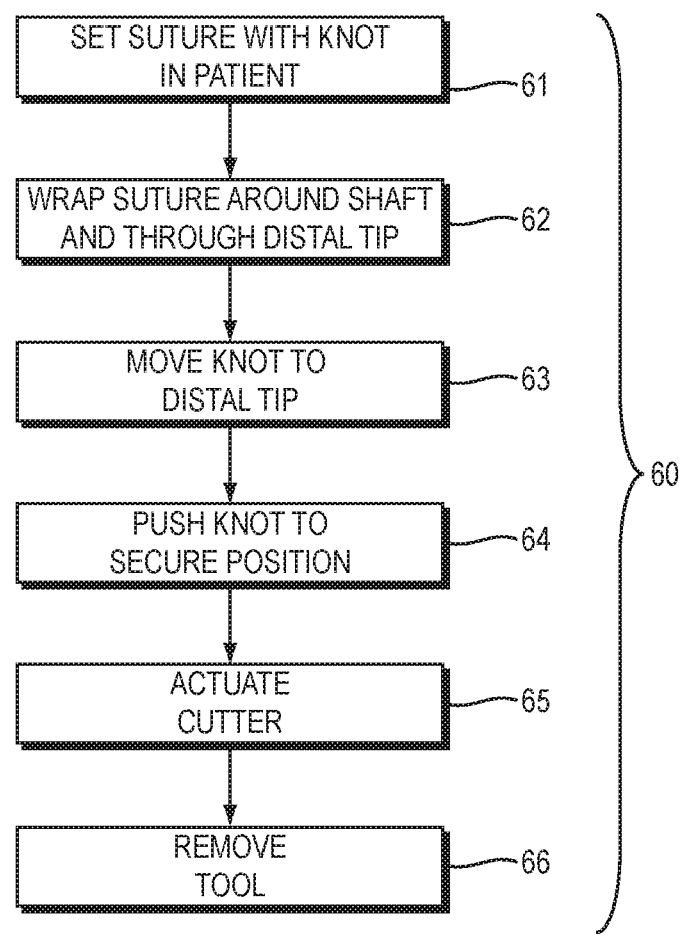
FIG. 6 is a flow chart providing an exemplary process for using the instrument of FIG. 1.

FIG. 6 provides an exemplary method for operation of the knot pusher and suture cutter 60. In a first step 61, the surgeon will set suture that includes a slip knot in the patient. Techniques for setting suture including slip knot are known, and are not described in this disclosure. In a second step 62, the suture is wrapped around the shaft of the instrument, encouraged into the side-loading channel and out through the cannulation in the knot retainer. In a third step 63, the slip knot is pulled into the knot retainer. In a fourth step 64, the slip knot is pushed into position and secured by the knot pusher. In the fifth step 65, once the slip knot has been secured, the cutter is actuated. In a sixth step 66, the instrument is removed from the patient.

Having thus introduced an exemplary embodiment of the instrument 10 some additional aspects are now provided.

Generally, the instrument 10 may be fabricated from any materials deemed appropriate. For example, the instrument 10 may include: polyether ether ketone (PEEK), which is a colorless organic thermoplastic polymer in the polyaryletherketone (PAEK) family; poly(methyl methacrylate) (PMMA); NYLON (available from DuPont chemical of Wilmington Del.), which is a polyamides type of polymer; polyethylene; poly propylene; poly styrene; polyvinyl chloride and other such materials. Polymer-based materials may be particularly useful for components such as the shell 41, the body 32, the thumb latch 42 and the plug 35.

Additionally, metal or metallic components may be used. The metal may be any one of a variety of alloys (for example, a steel alloy), or a substantially pure elemental metal (such as aluminum). Metallic components may include dispersions of metal particulate within another matrix such as a polymer. Metal or metallic materials may be particularly useful for components such as the cutting sleeve 5 in the knot pusher 7.

Other materials such as rubber may be used. Soft materials, such as those formed with rubber, may be particularly useful for any gaskets desired as well as, for example, incorporation of a removable plug 35.

Generally, the knot pusher 7 extends some distance beyond the distal tip of the cutting sleeve 5. The actual length of the cutting sleeve as well as the knot pusher 7 may be varied.

In some embodiments, the cutting sleeve 5 remain stationary relative to the handle 1. Actuation of the control 3 causes the knot pusher 7 to move in a proximal direction.

In some embodiments, the knife 24 includes a straight edge. In some other embodiments, the knife 24 includes a shaped edge such as one to encourage the suture into a central position (as shown in FIG. 2B).

The instrument 10 may be manufactured as a disposable device. Alternatively, the instrument 10 may be provided as a user serviceable device that may be sterilized between uses.

The instrument 10 may be sized for the needs of the patient, as well as the particular type of suture in use. More specifically, a length of the shaft may be varied, a width of the side-loading channel 11 may be varied and other such parameters may be varied as deemed appropriate.

Standards for design, fabrication and performance of the instrument 10 are to be determined according to the needs of a designer, manufacturer, user or other similarly interested party. Aspects presented herein are merely illustrative and are not to be construed as limiting.

Various other components may be included and called upon for providing for aspects of the teachings herein. For example, additional materials, combinations of materials and/or omission of materials may be used to provide for added embodiments that are within the scope of the teachings herein.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for securing a suture comprising a knot, the method comprising:
    selecting an instrument, the instrument comprising:
        a shaft comprising:
            a cannula having a proximal portion coupled to a handle and a distal portion including a distal end, the cannula extending parallel with a longitudinal axis of the handle, the cannula extending through a distal end of the handle to define a cannulated tip of the shaft; and
            a cutting sleeve movably disposed over the cannula and configured to slide over the cannula;
        a side-loading channel disposed along a side of the distal portion of the cannula and extending through the distal end of the cannula; and
        a user manipulable control portion slidably mounted on an upper surface of the handle, the user manipulable control portion configured for controlling axial movement of the cutting sleeve along the cannula;
    loading the suture into the side-loading channel; and
    securing the suture within the side-loading channel.

2. The method as in claim 1, wherein loading the suture into the side-loading channel comprises wrapping the suture around the instrument and into the side-loading channel.

3. The method as in claim 1, further comprising actuating the cutting sleeve to cut the suture by sliding the user manipulable control portion along the surface of the handle.

4. The method as in claim 1, wherein the side-loading channel comprises a helical channel extending through a sidewall of the cannula.

5. The method as in claim 4, wherein the side-loading channel comprises a longitudinal channel portion parallel to the longitudinal axis of the handle and intersecting the helical channel.

6. The method as in claim 1, wherein the distal end of the cannula comprises a knot pushing surface configured to retain a knot in the suture.

7. The method as in claim 6, wherein the knot comprises a slip knot.

8. The method as in claim 6, further comprising setting the suture including the knot in a patient.

9. The method as in claim 1, wherein the cannulated tip of the shaft is configured for receiving the suture from the side-loading channel.

10. The method as in claim 1, wherein the cannulated tip of the shaft comprises a cutting surface for cutting the suture.

11. The method as in claim 1, wherein the cutting sleeve comprises a knife edge configured for cutting the suture.

12. The method as in claim 1, wherein the cutting sleeve comprises at least one aperture configured to pass debris.

* * * * *